United States Patent [19]

Bornstein

[11] 4,029,782

[45] June 14, 1977

[54] CEFAZOLIN SUSPENSION FOR PARENTERAL ADMINISTRATION

[75] Inventor: Michael Bornstein, Indianapolis, Ind.

[73] Assignee: Eli Lilly and Company, Indianapolis, Ind.

[22] Filed: Apr. 28, 1975

[21] Appl. No.: 573,283

[52] U.S. Cl. .................................. 424/246; 424/80; 424/307

[51] Int. Cl.² ............................................. A61K 31/54

[58] Field of Search ........................................ 424/246

[56] References Cited

UNITED STATES PATENTS

| | | | |
|---|---|---|---|
| 3,293,133 | 12/1966 | Hill | 424/246 X |
| 3,296,258 | 1/1967 | Vischer et al. | 424/246 X |
| 3,297,692 | 1/1967 | Flynn | 424/246 X |
| 3,516,997 | 6/1970 | Takano et al. | 260/243 |
| 3,652,570 | 3/1972 | Gittos et al. | 424/246 X |
| 3,897,423 | 7/1975 | Treuner et al. | 424/246 X |

OTHER PUBLICATIONS

Remington's Pharmaceutical Sciences, 1965, 13th Edition, pp. 627 to 640.

*Primary Examiner*—Dale R. Ore
*Attorney, Agent, or Firm*—Ralph W. Ernsberger; Everet F. Smith

[57] ABSTRACT

A pharmaceutical suspension for parenteral administration is provided which comprises finely divided crystals of cefazolin suspended in a vehicle composed of water, a pharmaceutically acceptable surfactant, lecithin and a viscosity adjusting agent or agents. Methods are also provided for preparing such a suspension.

20 Claims, No Drawings

CEFAZOLIN SUSPENSION FOR PARENTERAL ADMINISTRATION

BACKGROUND OF THE INVENTION

1. Field of Invention

This invention is concerned with a pharmaceutical dosage form. More particularly, the instant invention involves a pharmaceutical suspension of cefazolin for parenteral administration.

2. Prior Art

The cephalosporins constitute an important class of semisynthetic antibiotics that have proved highly useful in treating bacterial infections in man. Cefazolin is one of this class. Some of the cephalosporins are administered orally, some parenterally, and others are useful both orally and parenterally. Presently, cefazolin is administered parenterally for a variety of respiratory, genito-urinary and other infections. It is particularly effective against *Staphylococcus aureus*.

Currently, cefazolin is administered as a solution of its sodium salt; cefazolin sodium being very soluble in water. One of the significant problems with the administration of a cefazolin sodium solution is the pain and irritation experienced by the patient at the site of the injection. Moreover, the blood levels which develop after an injection of cefazolin sodium are of relatively short duration, requiring frequent injections to maintain a therapeutic cefazolin blood level.

Cefazolin, an acid in its unmodified form, has a relatively low solubility in water; something in the order of 3.0 mg/ml. And, a number of antibiotics having low water solubilities; namely penicillins such as the procaine and the benzathine forms, have been prepared as pharmaceutically acceptable suspensions for parenteral administration (I.M.). A variety of formulations have been used over the past three decades. All have been preparations in which finely divided particles have been suspended in a vehicle comprised of water and one or more of wetting agents, suspending agents, emulsifiers, viscosity adjusting agents, preservatives, buffers, and the like. Generally, these adjuncts have been present in various combinations and widely diverse concentrations. All these pharmaceutical aids (a U.S.P. description) have the approval of the United States Pharmacopeia, National Formulary, Food Chemicals Codex, or the Food and Drug Administration after the safety has been established for the purpose.

Accordingly, it is an object of this invention to provide a pharmaceutical suspension of cefazolin for parenteral administration utilizing pharmaceutically approved ingredients that induce a minimum of pain and irritation when injected intramuscularly.

It is another object of this invention to provide a cefazolin suspension that induces a prolongation of therapeutic blood levels on intramuscular injection.

SUMMARY

It has now been discovered that the pain and irritation experienced on the intramuscular (I.M.) injection of cefazolin as the sodium salt can be significantly reduced by the IM administration of cefazolin in a pharmaceutical suspension comprised as follows: (a) Cefazolin particles which are of a size wherein at least 80 percent are $<10 \mu m$ and all are $<100 \mu m$. And, (b) a vehicle comprised of water, a pharmaceutically acceptable surfactant, lecithin and a viscosity adjusting agent selected from the group consisting of providone and sodium carboxymethylcellulose or a combination thereof. Therapeutic blood levels are also maintained for a significantly longer interval.

A suitable method of preparing such a suspension comprises formulating the vehicle, sterilizing such vehicle by autoclaving, cooling such sterilized vehicle to room temperature and combining previously sterilized finely divided cefazolin particles therewith with vigorous agitation.

DESCRIPTION OF THE PREFERRED EMBODIMENT

One aspect of this invention relates to a novel pharmaceutical suspension for parenteral administration (I.M.) which comprises a ready-to-use suspension of cefazolin. This novel pharmaceutical suspension is comprised of: a) finely divided cefazolin; b) lecithin; c) a pharmaceutically acceptable surfactant; d) water; and e) a viscosity adjusting agent selected from the group consisting of providone and sodium carboxymethylcellulose or a combination thereof.

Cefazolin is a member of the class of antibiotics generically described as cephalosporins. It is synthesized from the cephalosporin derivative, 7-ACA, (7-aminocephalosporanic acid). It is represented by the following structural formula:

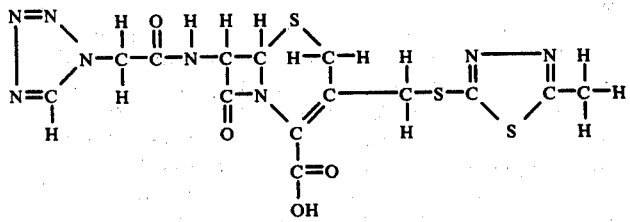

The accepted chemical name for cefazolin is 3-[[5-methyl-(1,3,4-thiadiazol-2-yl)-thio]-methyl]-7-[2-(1H-tetrazol-1-yl)acetamido]-3-cephem-4-carboxylic acid. It is marketed around the world as the sodium salt. Cefazolin is indicated in the treatment of respiratory tract infections due to *D. pneumoniae*, *Klebsiella spp.*, and others; genito-urinary tract infections due to *E. coli*, *Proteus mirabilis*, *Klebsiella spp.*, and others; and *Staph. aureus* infections in general.

The cefazolin utilized in the instant invention is aseptically crystallized from a hydro-organic solvent such as water-isopropanol, and after drying, the crystals are reduced to a particle size where 80 percent are $<10$ $\mu m$ and all are below $<100$ $\mu m$.

The useful pharmaceutical suspension of this invention can contain from about 10 to about 65 percent (W/V) of cefazolin. Actually a satisfactory suspension can be achieved with less than 10 percent of the active agent, but there would be no reasonable pharmaceutical use for such a low concentration. In fact, only rarely will a 10 percent suspension be found to be pharmaceutically desirable. For convenience of administration a suspension containing either about 25 percent (250 mg/ml) or 50 percent (500 mg/ml) (W/V) is preferred. And of these two, a 50 percent suspension of cefazolin is especially preferred. Suspensions containing more than 65 percent (650 mg/ml) are pharmaceutically possible, but are not recommended because such preparations are usually very viscous and are not considered desirable for injection.

The particle size of the cefazolin crystals can be varied, but it will be apparent to those skilled in the art that crystals that are too small will tend to increase the viscosity of the suspension and those that are too large will increase the chance of a plugged needle when an injection of the suspension is being given. Consequently, the specification for the particle size that 80 percent are <10 μm and all are <100 μm is a compromise to hold the viscosity at a reasonable level without permitting large boulder-sized particles in the suspension that will possibly plug a 20 gauge needle.

Lecithin is included in the suspension as a suspending agent. It is an essential ingredient to aid in resisting packing of the crystals on prolonged storage of the suspension without agitation. It is also useful as an antioxidant adding to the chemical stability of the suspension. The specifications for lecithin can be found on page 444 et seq of Food Chemicals Codex, 2nd Edition, National Academy of Sciences, Washington, D.C. (1972).

In the novel pharmaceutical suspension of this invention, lecithin can be present in amounts of from about 0.1 to about 1.0 percent (W/V) of the suspension. The actual amount of lecithin utilized is roughly proportional to the concentration of the cefazolin. When the especially preferred concentration of 50 percent (W/V) of cefazolin is contained in the suspension, the preferred amount of lecithin is about 0.5 percent (W/V).

A pharmaceutically acceptable surfactant is another essential ingredient in the useful suspension of this invention. Inasmuch as the instant suspension is provided in a water vehicle, an essentially water soluble surfactant is required. Listed among the pharmaceutically acceptable surfactants which have been found to be useful in the novel suspension of the present invention are polyoxyethylene (20) sorbitan monolaurate (polysorbate 20), polyoxyethylene (20) sorbitan monostearate (polysorbate 60) polyoxyethylene (20) sorbitan monooleate (polysorbate 80), polyoxyl 40 stearate, polyoxyethylene 50 stearate, sodium lauryl sulfate, and the like. The preferred pharmaceutically acceptable surfactant is polyoxyethylene (20) sorbitan monooleate. The surfactant can be employed in concentration from about 0.1 to about 1.0 percent (W/V) of the suspension. Preferably, the surfactant concentration is about 0.3 percent (W/V) of the suspension. The use of the surfactant in the amounts indicated is required to assure a complete wetting of the particles of cefazolin. Moreover, the presence of the surfactant aids in establishing zeta forces surrounding such particles which tend to discourage agglomeration of the particles and retard settling of the suspension. It will be understood by those skilled in the art that optimum quantities of surfactants are important to prepare stable suspensions, but that extra amounts are of no particular use although no mischief results therefrom. Consequently, excess amounts of surfactants are of no particular benefit and do add to the cost of preparing the suspension.

In addition to the lecithin and the pharmaceutically acceptable surfactant which are required in the pharmaceutical suspension of this invention, a viscosity adjusting agent is also needed to provide a suspension in which the settling of the particles is impeded and at the same time remains sufficiently fluid to be syringeable. By syringeable it is meant that the suspension can be withdrawn easily from an ampoule into a 5cc syringe with a 20 gauge needle and subsequently injected from such a syringe through the 20 gauge needle into muscle tissue.

Viscosity adjusting agents which are useful in the present invention include povidone and sodium carboxymethylcellulose. The specifications for both of these agents are to be found in the United States Pharmacopeia (U.S.P.) XIX, (1975) pages 395 and 71, respectively. In this invention these two agents can be used independently or in any combination. However, one or the other, or both, are required in amounts which provide a concentration of viscosity adjusting in the suspension of from about 0.1 to about 2.0 percent (W/V). Preferably, with a cefazolin concentration of about 50 percent (W/V) in the suspension, about 0.5 percent (W/V) of the viscosity adjusting agent is utilized. Especially preferred in the novel suspension of this invention is a concentration of 0.25 percent (W/V) of each of the povidone and the sodium carboxymethylcellulose.

The water vehicle utilized in the instant invention is water for injection, the specifications for which are detailed on pages 539–40, U.S.P. XIX (ibid). Up to 90 percent of the total suspension can be water with the actual amount depending upon concentration of the cefazolin in the suspension. Good pharmaceutical practice permits the definition of the amount of water in a suspension to be: q.s. 100 percent by volume. And those skilled in the art will readily understand such terminology. Because the absolute density of particles suspended in water can be (and usually is) greater than one, and because such materials as lecithin, povidone, sodium carboxymethylcellulose, surfactants, et al. often do not exhibit a 1:1 weight to volume ratio when added to water, any other way of specifying the water concentration could result in the sum of the parts adding up to more or less than one-hundred percent (W/V). It is also to be understood that in designating the concentration of the various ingredients on a (W/V) basis consistent units are equated, in other words 1g equated with 1 ml, and so on.

The novel pharmaceutical suspension of this invention can be comprised of from about 10 to about 65 percent (W/V) of the cefazolin, from about 0.1 to about 1.0 percent (W/V) of the lecithin, from about 0.1 to about 1.0 percent (W/V) of the pharmaceutically acceptable surfactant, from about 0.1 to about 2.0 percent (W/V) of the viscosity adjusting agent selected from the group consisting of povidone and sodium carboxymethylcellulose or a combination thereof, and water q.s. to 100 percent by volume.

The preferred composition of the novel pharmaceutical suspension of this invention comprises: a) about 50 percent (W/V) of cefazolin, b) about 0.5 percent (W/V) of lecithin, c) about 0.3 percent (W/V) of a pharmaceutically acceptable surfactant, d) about 0.5 percent (W/V) of a viscosity adjusting agent selected from the group consisting of povidone and sodium carboxymethylcellulose or a combination thereof, and
e) water q.s. to 100 percent by volume.

It is to be understood that, along with the water for injection, all of the ingredients contained in the vehicle of the above-described pharmaceutical suspension are sterilized before sterile cefazolin is combined therewith to form the suspension. Moreover, the process of preparing the useful pharmaceutical suspension of this invention is to be carried out using appropriate sterile (aseptic) procedures. Such procedures are well-known to those skilled in the art; and reference can be made to U.S.P. XIX, pages 709 et seq. (ibid) for further details.

In addition to the ingredients contained in the novel pharmaceutical suspension of the instant invention detailed hereinbefore, preservatives, such as one or more of the parabens (butyl, ethyl, methyl and propyl), pages 553, 557, 561 and 568, respectively, of U.S.P. XIX (ibid), can be added to the composition. For example, a preferred preservative composition of about 0.056 percent methylparaben and about 0.006 percent propylparaben is combined with the especially preferred composition of this invention. While it constitutes good pharmaceutical practice to include these preservatives in this useful cefazolin suspension, such are not required and form no part of the instant invention.

Another aspect of this invention relates to the process for preparing the useful pharmaceutical suspension having the composition described hereinabove.

The process by which the novel pharmaceutical suspension detailed hereinbefore is prepared comprises the following steps:
 a. The sterile cefazolin crystals are reduced in particle size to a specification wherein at least 80 percent are $<10$ $\mu$m and all are $<100$ $\mu$m.
 b. An appropriate quantity of water for injection is heated to about 80° C. in a suitable vessel equipped with means for agitation.
 c. A pharmaceutically acceptable surfactant is combined with agitation, with the warm water for injection.
 d. Lecithin is added, with agitation, to the preparation from (c).
 e. A viscosity adjusting agent selected from the group consisting of povidone and sodium carboxymethylcellulose, or a combination thereof, is added, with agitation, to the preparation from (d).
 f. The preparation from (e) is sterilized by autoclaving for about 60 minutes at 115° to 125° C. and about 20 psig.
 g. The sterilized preparation from (f) is cooled to room temperature.
 And, (f) the desired quantity of cefazolin from (a) is added aseptically, with agitation, to the preparation from (g).
 The pharmaceutical preparation thus prepared can be filled aseptically into previously sterilized vials or syringes of whatever size and in whatever amounts are desired.

The reduction of the particle size of the cefazolin in step (a) can be achieved by grinding the crystals in a high energy hammer mill; such as a Fitzpatrick Mill; an attrition mill, such as a Schultz O'Neil Mill; or a high pressure air mill. Sterile procedures, such as those described in U.S.P. XIX (ibid), are required to avoid bacterial and fungal contamination in the grinding operation. It was found that the best results could be achieved by two passes through an air mill running at about 60–90 psig. Those skilled in the art will understand the operation of the equipment and the aseptic procedures needed to accomplish this step in the process.

The vehicle utilized in the useful process of this invention is water for injection, U.S.P. Such water need not be sterile for use in the process, as an autoclaving step after all of the ingredients except the cefazolin are added achieves this condition. However, the water must meet the U.S.P. test for pyrogens.

The specifications for the lecithin, povidone and sodium carboxymethylcellulose and a discussion of pharmaceutically acceptable surfactants are all included hereinbefore.

In the process of preparing the pharmaceutical suspension of cefazolin for parenteral administration, from about 35 to about 90 parts by volume of water for injection are placed in a suitable vessel and heated to about 80° C. The amount of water utilized can be varied inversely with the concentration of cefazolin desired in the final suspension. For the highest concentration of cefazolin, about 65 percent (W/V), 35 parts of water, by volume, is about the maximum quantity which can be used. It will be recognized that as the desired final concentration of cefazolin in the suspension is reduced, the amount of water utilized in starting the process can be increased, and good pharmaceutical practices indicate that such should be done. However, it is not necessary to do so as the q.s. to 100 percent by volume after the addition of the cefazolin will provide the required water content of the suspension. It was found that when a suspension containing about 50 percent (W/V) (500 mg/ml) of cefazolin was started utilizing about 35 parts by volume of the water, the resulting process was pharmaceutically satisfactory. Moreover, the smaller the amount of complete vehicle utilized, the easier the materials handling requirement of the sterilization step.

The preferred process involves the addition of the pharmaceutically acceptable surfactant to the water prior to the addition of the lecithin and the viscosity adjusting agent. And, inasmuch as it is essential that the water to which the lecithin is added should be at about 80° C. to facilitate its dispersion therein, it is preferred that the water be heated to about 80° C. before the surfactant is added thereto.

The addition of the pharmaceutically acceptable surfactant, lecithin and viscosity adjusting agent should, in every case, be accompanied by agitation until the mixing and/or dispersion is complete.

After all of the vehicle modifying agents discussed above have been added, mixed and dispersed in the water, the preparation is sterilized. Autoclaving is a completely satisfactory sterilizing method and should be carried out for about 60 minutes at 115° to 125° C. and about 20 psig. It goes without noting that heat without pressure is not a satisfactory sterilizing method as the water will boil away. Even at 20 psig in the autoclave there will be a little water loss, but not enough to be troublesome in the 60 minutes to which the preparation is exposed to the 115° C. to 125° C. temperature.

Following the sterilization of the modified vehicle, it is highly desirable to allow such vehicle to come to room temperature before the cefazolin is added thereto. Once the vehicle has arrived at room temperature, the cefazolin can be added then, or the vehicle can be set aside in dead storage for a reasonable time before the active agent is added. When the latter option is exercised, care must be taken to maintain the sterility of the vehicle before it is used. Once again U.S.P. XIX (ibid) discusses appropriate procedures to be followed in this event.

Alternatively, a modified vehicle preparation procedure calls for admixing the pharmaceutically acceptable surfactant and the viscosity adjusting agent with the water for injection in that order and at room temperature, with agitation, of course. Then such a preparation is sterilized by autoclaving under the conditions detailed hereinbefore. Following the autoclaving step, the sterilized modified vehicle is cooled to about 80° C. and at that time a previously sterilized lecithin is added to such vehicle and dispersed therein with agitation. Following the lecithin addition, the preparation is allowed to cool to room temperature before adding the cefazolin thereto.

When preservatives, such as the parabens described hereinbefore are to be added to the pharmaceutically acceptable suspension, such addition is made before the sterilization step, irrespective of whether the the preferred or alternative modified vehicle preparation procedure is followed. In any event, it is preferred to add the preservative before the surfactant has been mixed with the water.

The admixing of the finely divided cefazolin can be accomplished best by slowly adding the insoluble crystals to a vigorously agitating vehicle. The particles are slow to wet and an addition of a large quantity of solids to the vehicle at one time will tend to promote agglomeration which will require considerable time and mixing energy to disperse.

The quantities of the various ingredients which make up the useful pharmaceutical suspension of the present invention, having been detailed explicitly hereinbefore, the preferred process for preparing such a suspension comprises: (a) combining, with agitation, from about 0.1 to about 1.0 part by weight of a pharmaceutically acceptable surfactant with about 35 parts by volume of water for injection, said water having been heated to about 80° C.; (b) adding to the preparation from (a), with agitation, from about 0.1 to about 1.0 part by weight of lecithin; (c) adding to the preparation from (b), with agitation, from about 0.1 to about 2.0 parts by weight of a viscosity adjusting agent selected from the group consisting of povidone and sodium carboxymethylcellulose or a combination thereof; (d) sterilizing the preparation from (c) by autoclaving for about 60 minutes at 115° to 125° C. and about 20 psig; (e) cooling the preparation from (d) to room temperature; (f) adding to the preparation from (e), with agitation, from about 10 to about 65 parts by weight of sterile cefazolin previously reduced to particles having a size wherein at least 80 percent are <10 $\mu$m and all are <100 $\mu$m; and, (g) adding to the preparation from (f), with agitation, sufficient sterile water for injection, U.S.P. to q.s. said suspension to 100 parts by volume.

The especially preferred process for preparing the novel pharmaceutical suspension of cefazolin for parenteral administration of the present invention comprises: (a) combining, with agitation, about 0.3 parts by weight of a pharmaceutically acceptable surfactant with about 35 parts by volume of water for injection, said water having been previously heated to about 80° C.; (b) adding to the preparation from (a), with agitation, about 0.5 parts by weight of lecithin; (c) adding to the preparation from (b), with agitation, about 0.5 parts by weight of a viscosity adjusting agent selected from the group consisting of povidone and sodium carboxymethylcellulose or a combination thereof; (d) sterilizing the preparation from (c) by autoclaving for about 60 minutes at 115° to 125° C. temperature and 20 psig; (e) cooling the preparation from (d) to room temperature, (f) adding to the preparation from (e), with agitation, about 50 parts by weight of sterile cefazolin previously reduced to particles having a size wherein at least 80 percent are <10 $\mu$m and all are <100 $\mu$m; and, (g) adding to the preparation from (f) sufficient sterile water for injection U.S.P. to q.s. said suspension to 100 parts by volume.

The embodiments of this invention are further illustrated by the following example:

EXAMPLE I

Preparation of Cefazolin Suspension Containing 0.5 g Antibiotic Activity per Milliliter.

Five liters of water for injection were placed in a suitable vessel equipped with means for vigorous agitation, and the temperature of the water raised to 80° C. Five and six-tenths grams of methylparaben and 0.6 g of propylparaben were added to the warm water with agitation which was continued until the solution was clear. Next, 24.8 g of polysorbate 80 were added to the 80° paraben-water preparation, followed by 24.8 g of sodium carboxymethylcellulose and 24.8 g of povidone. Vigorous agitation of the mixture was continued until dispersion was complete, and then 46.4 g of lecithin were added with agitation to complete the formulation of the vehicle for the suspension. The vessel containing the thus prepared vehicle was placed in an autoclave and sterilized for 60 minutes at about 121° C. and about 20 psig. Following the autoclaving, the vessel containing the sterilized vehicle was removed and cooled overnight to room temperature.

To the cooled and sterile vehicle were added slowly with very vigorous agitation 5,330 g of sterile cefazolin having a particle size wherein better than 90 percent were <10 $\mu$m and all were <100 $\mu$m. The quantity of cefazolin indicated contained a 12 percent excess. After the cefazolin was completely dispersed in the vehicle, the volume of the suspension was q.s. 'd to 10 liters by adding approximately 1.066 liters of sterile water for injection U.S.P. and agitation was continued for about an hour. The addition of the cefazolin and the sterile water for injection was carried out following accepted aseptic processing procedures as detailed in U.S.P. XIX (ibid).

The suspension of cefazolin prepared as detailed above had an indicated density of about 1.210 g/ml, and assayed 554 mg/ml.

The useful pharmaceutical suspension of cefazolin of this invention was shown to be significantly less irritating on injection than its counterpart cefazolin sodium solution. The commercial product of today is cefazolin sodium which is water soluble and is administered parenterally as a solution. When equal 0.5 g quantities of antibiotic activity were administered as cefazolin sodium solution and cefazolin suspension by injecting a 1 ml total dose in the gluteus muscle of the rabbit, the average volume of inflamed muscle for cefazolin sodium was 4.29 cc as compared with 2.26 cc for cefazolin. Each of the preparations were injected into the same rabbit, one in the right hip and the other in the left. Twenty-four hours later the rabbit was sacrificed and the inflamed muscle from each site was excised and the normal tissue was pared away. The mass of inflamed tissue was then added to 50 ml of water in a 100 ml graduate and the volume of water displaced was read as the volume of inflamed tissue. This relative test indicated almost a 50 percent reduction in irritation for the cefazolin suspension as compared to cefazolin sodium injection.

Moreover, on injection, the cefazolin suspension proved to be a longer acting form of the antibiotic than cefazolin sodium. For example, when the cefazolin suspension of this invention was compared for duration of blood levels in dogs with cefazolin sodium, measurable blood levels of cefazolin activity persisted for more than twice as long. Two groups of six each of female beagle dogs were injected with 10 mg/kg of cefazolin activity. One group was given cefazolin suspension and the other was injected with cefazolin sodium solution. The following tables shows the blood levels in mcg/ml at the indicated interval after injection.

TABLE I

Canine Blood Levels Cefazolin Activity Mcg/ml.

| Form Administered on Parenteral Injection | Time after Injections (hours) | | | | | | |
|---|---|---|---|---|---|---|---|
| (I.M.) | 0.5 | 1 | 1.5 | 2 | 3 | 4 | 6 |
| Cefazolin Suspension | 3.6 | 7.1 | 8.3 | 9.7 | 8.2 | 6.0 | 3.5 |
| Cefazolin Solution | 25.8 | 19.7 | 11.0 | 6.7 | 2.7 | N.A.* | |

*N.A. equals < 0.08 mg/ml

The data above clearly indicates the usefulness of the novel pharmaceutical suspension of cefazolin over the present product as the prolonged blood levels will permit a longer interval between injections, thereby reducing the number of injections required per day to maintain a therapeutic blood level in a patient to whom the cefazolin is being administered.

What is claimed is:

1. A pharmaceutical suspension for parenteral administration comprising from about 10 to about 65 percent (W/V) of cefazolin, from about 0.1 to about 1.0 percent of lecithin, from about 0.1 to about 1.0 percent (W/V) of a pharmaceutically acceptable surfactant, from about 0.1 to about 2.0 percent (W/V) of a viscosity adjusting agent selected from the group consisting of povidone and sodium carboxymethylcellulose or a combination thereof, and water for injection q.s. to 100 percent by volume.

2. The suspension of claim 1 wherein said pharmaceutically acceptable surfactant is polysorbate 80.

3. The suspension of claim 1 wherein said viscosity adjusting agent is povidone.

4. The suspension of claim 1 wherein said viscosity adjusting agent is sodium carboxymethylcellulose.

5. The suspension of claim 1 wherein a combination of povidone and sodium carboxymethylcellulose is utilized as the viscosity adjusting agent.

6. The suspension of claim 1 comprised of: a) about 50 percent (W/V) of the cefazolin, b) about 0.5 percent (W/V) of the lecithin, c) about 0.3 percent (W/V) of the pharmaceutically acceptable surfactant, d) about 0.5 percent (W/V) of the viscosity adjusting agent, and, e) water for injection q.s. to 100 percent by volume.

7. The suspension of claim 6 wherein the pharmaceutically acceptable surfactant is polysorbate 80.

8. The suspension of claim 6 wherein the viscosity adjusting agent is povidone.

9. The suspension of claim 6 wherein the viscosity adjusting agent is sodium carboxymethylcellulose.

10. The suspension of claim 6 wherein a combination of povidone and sodium carboxymethylcellulose is utilized as the viscosity adjusting agents.

11. A method of preparing a storage stable pharmaceutical suspension of cefazolin for parenteral administration comprising:
   a. combining, with agitation, from about 0.1 to about 1.0 parts by weight of a pharmaceutically acceptable surfactant with about 35 parts by volume of water for injection, U.S.P., said water having been previously heated to about 80° C.;
   b. adding to the preparation from a), with agitation, from about 0.1 to about 1.0 parts by weight of lecithin;
   c. adding to the preparation from b), with agitation, from about 0.1 to about 2.0 parts by weight of a viscosity adjusting agent selected from the group consisting of povidone and sodium carboxymethylcellulose or combination thereof;
   d. sterilizing the preparation from c) by autoclaving for about 60 minutes at 115° to 125° C. and 20 psig;
   e. cooling the preparation from d) to room temperature;
   f. adding to the preparation from e), with agitation, from about 10 to about 65 parts by weight of cefazolin previously reduced to a particle size wherein at least 80 percent are <10 μm and all are <100 μm; and
   g. adding to the preparation from f), with agitation, sufficient sterile water for injection, U.S.P. to q.s. said suspension to 100 party by volume.

12. The method of claim 11 wherein the pharmaceutically acceptable surfactant utilized in step a) is polysorbate 80.

13. The method of claim 11 wherein the viscosity adjusting agent utilized in step c) is povidone.

14. The method of claim 11 wherein the viscosity adjusting agent utilized in step c) is sodium carboxymethylcellulose.

15. The method of claim 11 wherein a combination of povidone and sodium carboxymethylcellulose is utilized in step c) as the viscosity adjusting agent.

16. The method of claim 11 comprising:
   a. combining, with agitation, about 0.3 parts by weight of the pharmaceutically acceptable surfactant with about 35 parts by volume of water for injection, U.S.P., said water having been previously heated to about 80° C.;
   b. adding to the preparation from a), with agitation, about 0.5 parts by weight of lecithin;
   c. adding to the preparation from b), with agitation, about 0.5 parts by weight of the viscosity adjusting agent;
   d. sterilizing the preparation from c) by autoclaving for about 60 minutes at 115° to 125° C. and 20 psig;
   e. cooling the preparation from d) to room temperature;
   f. adding to the preparation from e), with agitation, about 50 parts by weight of cefazolin previously reduced to a particle size wherein at least 80 percent are <10 μm and all are <100 μm; and
   g. adding to the preparation from f), with agitation, sufficient sterile water for injection, U.S.P. to q.s., said suspension to 100 parts by volume.

17. The method of claim 15 wherein the pharmaceutically acceptable surfactant utilized in step a) is polysorbate 80.

18. The method of claim 15 wherein the viscosity adjusting agent utilized in step c) is povidone.

19. The method of claim 15 wherein the viscosity adjusting agent utilized in step c) is sodium carboxymethylcellulose.

20. The method of claim 15 wherein the combination of povidone and sodium carboxymethylcellulose is utilized in step c) as the viscosity adjusting agent.

* * * * *